US009610101B2

(12) United States Patent
Tang et al.

(10) Patent No.: US 9,610,101 B2
(45) Date of Patent: Apr. 4, 2017

(54) LONG-BONE FRACTURE-REDUCTION ROBOT

(71) Applicants: Peifu Tang, Beijing (CN); Tianmiao Wang, Beijing (CN); Lei Hu, Beijing (CN); Lihai Zhang, Beijing (CN)

(72) Inventors: Peifu Tang, Beijing (CN); Tianmiao Wang, Beijing (CN); Lei Hu, Beijing (CN)

( * ) Notice: Subject to any disclaimer, the term of this patent is extended or adjusted under 35 U.S.C. 154(b) by 126 days.

(21) Appl. No.: 14/566,733

(22) Filed: Dec. 11, 2014

(65) Prior Publication Data

US 2015/0173819 A1 Jun. 25, 2015

Related U.S. Application Data

(63) Continuation of application No. PCT/CN2013/007459, filed on Apr. 12, 2013.

(30) Foreign Application Priority Data

Jun. 11, 2012 (CN) .......................... 2012 1 0191841

(51) Int. Cl.
*A61B 17/60* (2006.01)
*A61B 17/64* (2006.01)
(Continued)

(52) U.S. Cl.
CPC .......... *A61B 17/60* (2013.01); *A61B 17/6408* (2013.01); *A61B 17/66* (2013.01); *A61B 34/30* (2016.02)

(58) Field of Classification Search
CPC ...... A61B 17/60; A61B 17/6408; A61B 17/66
See application file for complete search history.

(56) References Cited

U.S. PATENT DOCUMENTS

2002/0061131 A1   5/2002   Sawhney et al.
2002/0122113 A1   9/2002   Foote
(Continued)

FOREIGN PATENT DOCUMENTS

CN   1561923 A    1/2005
CN   201492456 U  6/2010
(Continued)

OTHER PUBLICATIONS

International Search Report. PCT Application PCT/CN2013/074159, mailed Jan. 9, 2014 (With Translation).
(Continued)

*Primary Examiner* — David Bates
*Assistant Examiner* — Olivia C Chang
(74) *Attorney, Agent, or Firm* — Loza & Loza, LLP; Michael F. Fedrick

(57) ABSTRACT

A long-bone fracture-reduction robot is provided, and includes a machine base; a support slidably connected onto the machine base and able to move up and down; a plurality of electro-hydraulic drivers; and a six-degrees-of-freedom parallel robot arranged on the support, with the motion of the robot in six degrees of freedom hydraulically controllable using the plurality of electro-hydraulic drivers. The long-bone fracture-reduction robot includes two long-bone-fixing frames, one frame being coupled to the support and other being coupled to the six-degree-of-freedom parallel robot. The two long-bone-fixing frames are arranged to be side by side. Each of the two long-bone-fixing frames is fixedly connected to a corresponding mounting-and fixing plate.

10 Claims, 8 Drawing Sheets

(51) Int. Cl.
A61B 17/66 (2006.01)
A61B 34/30 (2016.01)

(56) References Cited

U.S. PATENT DOCUMENTS

| | | | |
|---|---|---|---|
| 2004/0061787 A1 | 4/2004 | Liu et al. | |
| 2004/0207831 A1 | 10/2004 | Aoyama | |
| 2005/0129325 A1 | 6/2005 | Wu | |
| 2007/0058879 A1 | 3/2007 | Cutler et al. | |
| 2007/0225704 A1* | 9/2007 | Ziran | A61B 17/66 606/57 |
| 2010/0312291 A1* | 12/2010 | Mast | A61B 17/6408 606/86 B |
| 2012/0041439 A1* | 2/2012 | Singh | A61B 17/62 606/54 |
| 2014/0379038 A1* | 12/2014 | Dogramadzi | A61B 17/62 606/86 R |

FOREIGN PATENT DOCUMENTS

| | | |
|---|---|---|
| CN | 101847182 A | 9/2010 |
| CN | 102715955 A | 10/2012 |
| WO | WO2014005457 | 1/2014 |

OTHER PUBLICATIONS

International Preliminary Report on Patentability, PCT Application PCT/CN2013/074159, mailed Dec. 16, 2014 (With Translation).

Dobbe, J.G.G., et al, "Computer-assisted and patient-specific 3-D planning and evaluation of a single-cut rotational osteotomy for complex long-bone deformities", Med Biol Eng Comput, vol. 49:pp. 1363-1370, 2011.

Du, Hailong, et al., "Advancing computer-assisted orthopaedic surgery using a hexapod device for closed diaphyseal fracture reduction," The International Journal of Medical Robotics and Computer Assisted Surgery (2014), published online in Wiley Online Library (wileyonlinelibrary.com).

Gosling, T., et al., "Robot-assisted fracture reduction: a preliminary study in the femur shaft," *Med Biol Eng Comput*.;43(1):115-20. Jan. 2005.

Joung, Sanghyun, et al., "A Robot Assisted Hip Fracture Reduction with a Navigation System", Proc. 2008 International Conference Medical Image Computing and Computer Assisted Intervention (MICCAI 2008), Part II, LNCS 5242, pp. 501-508, 2008.

Li, Changsheng, et al., "Accuracy Analysis of a Robot System for Closed Diaphyseal Fracture Reduction," Regular Paper, International Journal of Advanced Robotics Systems, Received Dec. 24, 2013; Accepted Aug. 27, 2014, Int J Adv Robot Syst, vol. 11:169, 2014.

Majidifakhr Kamran, et al, "Robotic Assisted Reduction of Femoral Shaft Fractures using Stewart Platform", *Studies in Health Technology and Informatics 2009*; 142: 177-9 177 *IOS Press*, 2009.

Mukherjee, S., et al., "Surgeon-instructed, Image-guided and Robot-assisted Long Bone Fractures Reduction," 1st International Conference on Sensing Technology, Palmerston North, New Zealand, Nov. 21-23, 2005.

Seide, Klaus, et al., "A Hexapod Robot External Fixator for Computer Assisted Fracture Reduction and Deformity Correction.". Int J. Medical Robotics and Computer Assisted Surgery; Vole. 1, No. 1 pp. 64-69, 2004.

Tang, Peifu. "Novel 3D Hexapod Computer-assisted Orthopaedic Surgery System for Closed Diaphyseal Fracture Reduction." *The International Journal of Medical Robotics and Computer Assisted Surgery* 8.1 (2012): 17-24.

Wang, T., et al., "A removable hybrid robot system for long bone fracture reduction." Bio-Medical Materials and Engineering, vol. 24 pp. 501-509, 2014.

Wang, S., "Motion planning and control simulation for robot assisted femur fracture reduction," Master of Philosophy Thesis, The University of Hong Kong, Aug. 2010.

Westphal, Ralf, Simon Winkelbach, Thomas Goesling, Markus Oszwald, Tobias Huefner, Christian Krettek and Friedrich Wahl (2008). Telemanipulated Long Bone Fracture Reduction, Medical Robotics, Vanja Bozovic (Ed.), ISBN: 978-3-902613-18-9, InTech, Retrieved Jul. 7, 2015 from: http://cdn.intechopen.com/pdfs-wm/669.pdf.

Westphal, R., et al., "3D Robot Assisted Fracture Reduction." Published 2006, retrieved Dec. 9, 2012 at www.cs.tubs.de/rob/literatur/download/rwe_2006_07_iser.pdf.

Ozwald, M., et al., "Robot-assisted fracture reduction using three-dimensional intraoperative fracture visualization: an experimental study on human cadaver femora." J. Orthop Res., Sep. 2010; 28(9); 1240-4.

Westphal, R., "Sensor-Based Surgical Robotics: Contributions to Robot Assisted Fracture Reduction." Dr. Ing. Dissertation, Published Aug. 2007, retrieved Dec. 10, 2014 at www.rob.cs.tu-bs.de/content/03-research/03.../rwe_2007_08_diss.pdf.

Ye, Ruihua, et al., "Development of a Six Degree of Freedom (DOF) Hybrid Robot for Femur Shaft Fracture Reduction" IEEE Proceedings of the 2008 IEEE International Conference on Robotics and Biomimetics, Bangkok, Thailand, Feb. 21-26, 2009.

* cited by examiner

LONG-BONE FRACTURE-REDUCTION ROBOT

RELATED PATENT APPLICATIONS

This invention is a continuation of International Application No. PCT/CN2013/074159 filed 12 Apr. 2013, and published as WO 2014/005457 A1. International Application PCT/CN2013/074159 claims benefit of priority of Chinese Patent Application No. 201210191841.6 filed 11 Jun. 2012, granted on 14 May 2014 as CN102715955. The contents of each of International Application No. PCT/CN2013/074159 and of Chinese Patent Application No. 201210191841.6 are incorporated herein by reference.

FIELD OF THE INVENTION

The invention relates to the technical field of medical appliances, in particular to a long bone fracture reduction robot.

BACKGROUND OF THE INVENTION

Traditional fracture open reduction is performed by a doctor by use of an appliance under a direct vision environment. After open resetting, rigid internal fixation or external fixation is adopted for fixing an affected limb. By adopting an open reduction treatment way, closed fracture is artificially turned into open fracture, and the chance of infection is increased. In the operation process, the blood circulation is likely to be destroyed, a necrotic area at the fracture end is increased, and delayed healing and even no healing is caused. Simultaneously, when in open reduction, the removal of hematoma will interfere with the self-repair capability of a human body and also affect the healing of the fracture.

An intramedullary nail technology and a minimally invasive steel plate fixation technology which have been developed till now can solve the open reduction problem, but in the operation process, X-ray irradiation needs to be performed continuously, and the radiation to the doctor and a patient is greater. In addition, according to the prior art, the reduction is performed under a two-dimensional information environment, so that the poor reduction is easily caused, and the problems of low operation stability and the like also exist.

SUMMARY OF THE INVENTION

Hereinafter, a brief summary of the invention is given out to provide a basic understanding of certain aspects of the invention. It should be understood that the summary is not an exhaustive summary with respect to the invention. It is not intended to determine the key or important parts of the invention or limit the scope of the invention. It only aims at giving out certain concepts in a simplified form to serve as a prelude of more detailed description in later discussion.

At least one object of the invention is to provide a long-bone fracture-reduction robot which is used for solving the problems that X-ray irradiation needs to be performed continuously in an operation, the radiation to a doctor and a patient is comparatively great, the reduction is poor and the operation stability is poor in the prior art.

A long-bone fracture-reduction robot comprises a machine base and plurality of electro-hydraulic drivers, wherein a support capable of moving up and down is slidably connected on the machine base, and a six-degree-of-freedom parallel robot is arranged on the support; and the six-degree-of-freedom parallel robot comprises multiple first hydraulic cylinders, the number of the first hydraulic cylinders is the same as the number of the electro-hydraulic drivers, and the multiple first hydraulic cylinders are in one-to-one driving connection with the multiple electro-hydraulic drivers.

The long-bone fracture-reduction robot provided by the invention can plan a movement track of the six-degree-of-freedom parallel robot according to a Computed Tomography (hereinafter referred to as CT) before an operation and precisely control the movement of an affected limb through the six-degree-of-freedom parallel robot so as to complete the reduction of the affected limb. Thus, by using the long-bone fracture-reduction robot to perform the reduction operation, only one CT scan is needed, so that the quantity of radiation to the doctor and the patient is reduced. In addition, the movement of the affected limb is controlled through the six-degree-of-freedom parallel robot, so that the reduction precision is high, and the operation stability is good.

These and other advantages of the invention will be more evident through the detailed description of the preferred embodiments of the invention in combination with the accompanying drawings.

BRIEF DESCRIPTION OF THE DRAWINGS

The invention can be better understood through the following description in combination with the accompanying drawings, wherein the same or similar reference numerals are used to represent the same or similar parts in all the accompanying drawings. The accompanying drawings, together with the following detailed description, are included in the specification, form one part of the specification and are also used for further illustrating the preferred embodiments of the invention and explaining the principles and the advantages of the invention. In the drawings.

Those of skill in the art should understand that elements in the accompanying drawings are only shown for simplicity and clarity and are unnecessarily drawn to scale. For example, the sizes of certain elements in the accompanying drawings may be enlarged relative to other elements so as to aid in improving the understanding of the embodiments of the invention.

DETAILED DESCRIPTION OF THE EMBODIMENTS

Hereinafter, the exemplary embodiments of the invention are described in detail in combination with the accompanying drawings. For clarity and concision, the specification does not describe all the features of practical implementations. However, it should be understood that, in the process of developing any practical embodiments, many implementation-specific decisions must be made to achieve the specific targets of developers, for example, be in line with those limiting conditions which are related to a system and businesses, and these limiting conditions may change with the different implementations. In addition, it also should be understood that, although the development work may be very complex and time-consuming, the development work is only a routine task for those of skill in the art having the benefit from the disclosure.

Here, it should be noted that, in order to prevent unnecessary details from obscuring the invention, only device structures and/or processing steps which are closely related to the scheme according to the invention are described in the accompanying drawings and the description, and the representations and the descriptions of parts and processing which are little related to the invention and known by those of ordinary skill in the art are omitted.

Figure 1:
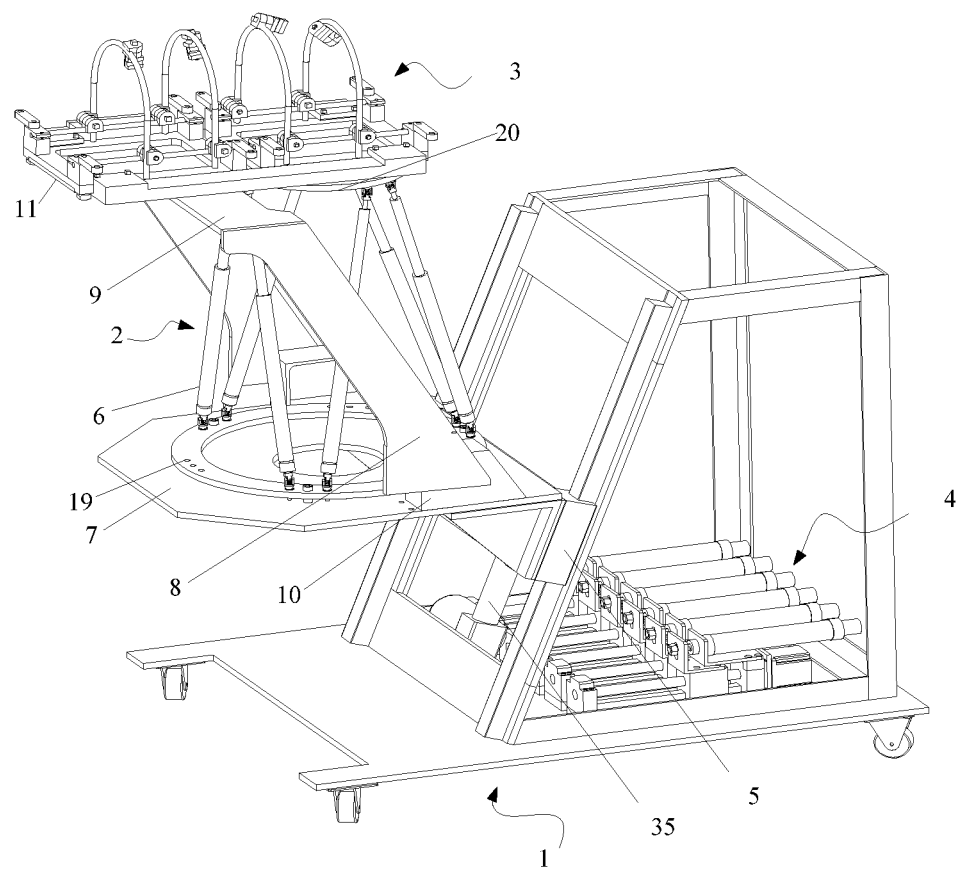
FIG. 1 is a perspective diagram of a long-bone fracture-reduction robot provided by an embodiment of the invention.

FIG. 1 is a perspective diagram of a long-bone fracture-reduction robot provided by an embodiment of the invention. As shown in FIG. 1, the long-bone fracture-reduction robot provided by the embodiment of the invention comprises a machine base 1 and plurality of electro-hydraulic drivers 4, a support 5 capable of moving up and down is slidably connected on the machine base 1, and a six-degree-of-freedom parallel robot 2 is arranged on the support 5. The six-degree-of-freedom parallel robot 2 comprises multiple first hydraulic cylinders 6. The number of the first hydraulic cylinders 6 is the same as the number of the electro-hydraulic drivers 4, and the multiple first hydraulic cylinders 6 are in one-to-one driving connection with the multiple electro-hydraulic drivers 4.

The long-bone fracture-reduction robot adopting the above scheme can plan a movement track of the six-degree-of-freedom parallel robot 2 according to a CT scan before an operation and precisely control the movement of an affected limb through the six-degree-of-freedom parallel robot 2 so as to complete the reduction of the affected limb. Thus, by using the long-bone fracture-reduction robot to perform the reduction operation, only one CT scan is needed, so that the quantity of radiation to a doctor and a patient is reduced. In addition, the movement of the affected limb is controlled through the six-degree-of-freedom parallel robot, so that the reduction precision is high, and the operation stability is good.

In actual use, the support 5 can be a welded steel structure and comprises a bottom plate 7, two support plates 8 which are parallel to each other and extend upwards are connected on the bottom plate 7 and a top plate 9 is welded between the top parts of the two support plates 8. The top plate 9 can be used as a stationary platform for placing a long-bone-fixing frame 3. In order to improve the connection stiffness and strength between the support plates 8 and the bottom plate 7, a support base 10 is welded between the support plates 8 and the bottom plate 7.

The electro-hydraulic drivers 4 are fixedly connected on the machine base 1.

The support 5 can move up and down along a track which is obliquely arranged on the machine base 1.

Figure 2:
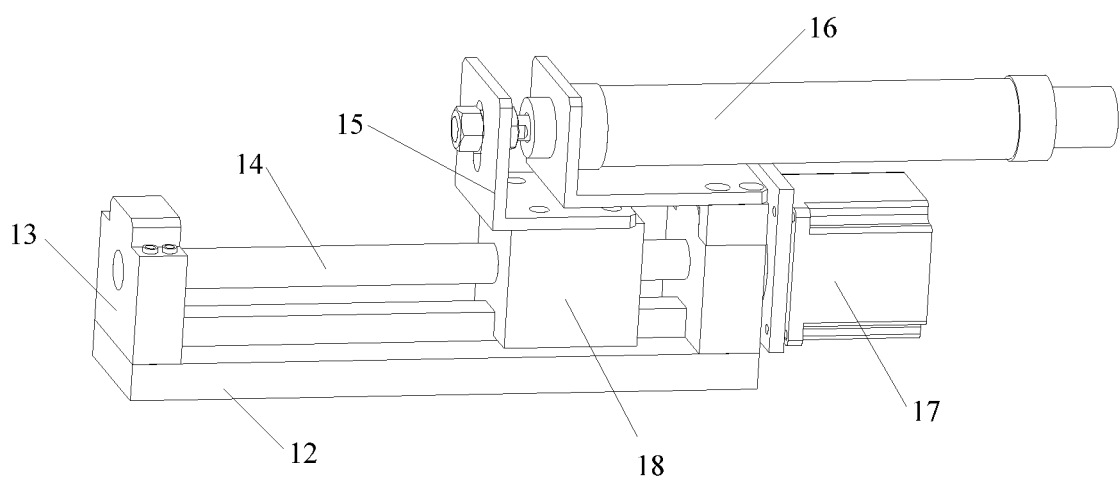
FIG. 2 is a perspective diagram of an electro-hydraulic driver provided by an embodiment of the invention.

Further, based on the above embodiment, FIG. 2 is a perspective diagram of the electro-hydraulic driver provided by the embodiment of the invention. As shown in FIG. 2, the electro-hydraulic driver 4 comprises a driving motor 17 and a second hydraulic cylinder 16, the driving motor 17 is in driving connection with a lead screw 14, a sliding block 18 is screwed on the lead screw 14, and a piston rod of the second hydraulic cylinder 16 is fixedly connected with the sliding block 18. The multiple first hydraulic cylinders 6 are in one-to-one connection with the multiple second hydraulic cylinders 16 through hydraulic pipelines, first oil (hydraulic fluid) ports 6-1 of the first hydraulic cylinders 6 are in one-to-one connection with and are in communication with first oil ports 16-1 of the second hydraulic cylinders 16, and second oil ports 6-2 of the first hydraulic cylinders 6 are in communication with second oil ports 16-2 of the second hydraulic cylinders 16.

In actual use, the six-degree-of-freedom parallel robot 2 comprises six first hydraulic cylinders 6, the six first hydraulic cylinders 6 are supported between a parallel mechanism fixing plate 19 and a parallel mechanism interface plate 20 which are arranged in a stacked manner, and the parallel mechanism interface plate 20 can be driven to perform six-degree-of-freedom motion in a space through coordinated actions of the six first hydraulic cylinders 6. In order to improve the motion precision of the six-degree-of-freedom parallel robot 2, the electro-hydraulic drivers 4 are respectively adopted for driving the first hydraulic cylinders 6 to telescope, and one electro-hydraulic driver 4 is connected with one first hydraulic cylinder 6 to realize one-to-one driving connection.

Specifically, each electro-hydraulic driver 4 comprises the driving motor 17 and the second hydraulic cylinder 16. The driving motor 17 can adopt, but not limited to a stepping motor. By adopting the stepping motor, the control precision can be improved, and the motion precision of the six-degree-of-freedom parallel robot 2 can be further improved. Each driving motor 17 is mounted on a base 12, two bearing seats 13 are mounted on the base 12, bearings are mounted in the two bearing seats 13, the lead screw 14 is mounted between the two bearing seats 13 through the bearings in a rotating manner, the lead screw 14 is connected with the driving motor 17, and the driving motor 17 drives the lead screw 14 to rotate. One sliding block 18 is screwed on each lead screw 14, and the sliding block 18 is in corresponding sliding fit with a sliding track on the base 12. The sliding block 18 is driven to perform linear motion along the sliding track through the rotation of the lead screw 14. A connecting frame 15 is fixedly connected on the sliding block 18 through a screw, the connecting frame 15 is fixedly connected with a piston rod of the second hydraulic cylinder 16, and a cylinder body of the second hydraulic cylinder 16 is fixedly connected on one of the bearing seats. The piston rod of the second hydraulic cylinder 16 is controlled to telescope through the motion of the sliding block 18. The first oil ports 6-1 of the first hydraulic cylinders 6 are in communication with the first oil ports 16-1 of the second hydraulic cylinders 16, and the second oil ports 6-2 of the first hydraulic cylinders 6 are in communication with the second oil ports 16-2 of the second hydraulic cylinders 16, so that the first hydraulic cylinders 6 and the second hydraulic cylinders 16 constitute a hydraulic transmission system, and the actions of the first hydraulic cylinders 6 are controlled by the actions of the second hydraulic cylinders 16. By adopting this driving way, the motion precision of the six-degree-of-freedom parallel robot 2 is improved, and the reduction precision of the operation is further improved.

Further, based on the above embodiment, two long-bone-fixing frames 3 are arranged on the six-degree-of-freedom parallel robot 2 and on the frame 5. The two long-bone-fixing frames 3 are used for fixing the affected limb.

In the operation process, one or more fixing nails are respectively driven into two ends of a fractured long bone, and the poses of the two sections of the fractured long bone are manually regulated by a doctor to perform preliminary reduction. Then, the two long-bone-fixing frames 3 are used for connecting the fixing nails, thereby fixing the affected limb on the long-bone-fixing frames 3. Wherein, one long-bone-fixing frame 3 is fixedly connected on the support 5 and kept still in the operation process, and the other long-bone-fixing frame 3 is fixedly connected on the parallel mechanism interface plate 20 of the six-degree-of-freedom parallel robot 2. The operations including translation, stretching, rotation and the like of the affected limb can be realized through the six-degree-of-freedom motion of the parallel mechanism interface plate 20 in the space.

Figure 3:
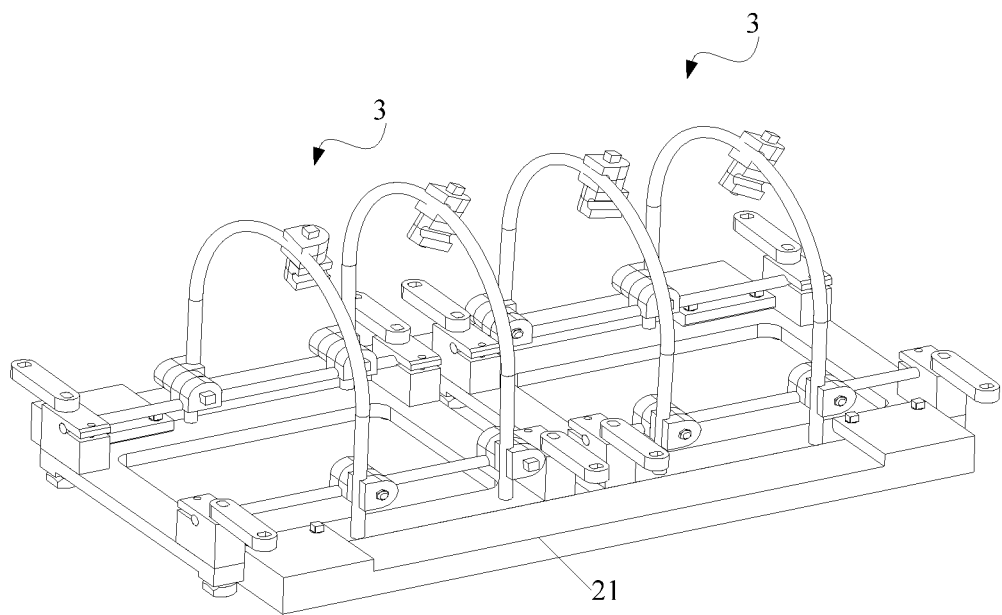
FIG. 3 is a perspective diagram of two long-bone-fixing frames provided by an embodiment of the invention after fixed connection.
Figure 4:
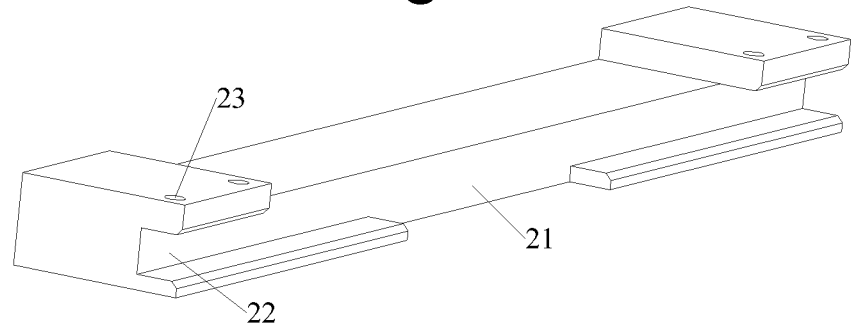
FIG. 4 is a perspective diagram of a mounting-and-fixing plate provided by an embodiment of the invention.

Further, based on the above embodiment, FIG. 3 is a perspective diagram of the two long-bone-fixing frames provided by the embodiment of the invention after fixed connection; and FIG. 4 is a perspective diagram of a mounting-and-fixing plate provided by the embodiment of the invention. As shown in FIG. 3 and FIG. 4, in order to improve the reduction precision, the mounting-and-fixing plates 21 are also included, and the two long-bone-fixing frames 3 are arranged side by side and fixedly connected with the mounting-and-fixing plates 21.

After the two long-bone-fixing frames 3 are connected with the affected limb, the two long-bone-fixing frames 3 are fixedly connected together through two mounting-and-fixing plates 21. After the two long-bone-fixing frames 3 are fixedly connected together, the CT scan is performed on the affected limb, then the affected limb in communication with the two long-bone-fixing frames 3 which are fixed together are correspondingly mounted on the long-bone fracture-reduction robot after the scan, and after that, the two mounting-and-fixing plates 21 are detached so as to enable one long-bone-fixing frame 3 to be capable of moving with the motion of the parallel mechanism interface plate 20. By adopting the mounting-and-fixing plates 21 to fix the two long-bone-fixing frames, the consistency between the pose of the affected limb during the CT scan and the pose of the affected pose after being mounted on the long-bone fracture-reduction robot can be ensured, and the long-bone fracture-reduction robot can control the motion of the six-degree-of-freedom parallel robot 2 by a path which is planned according to the CT scan result and realize the reduction of the affected limb.

Figure 5:
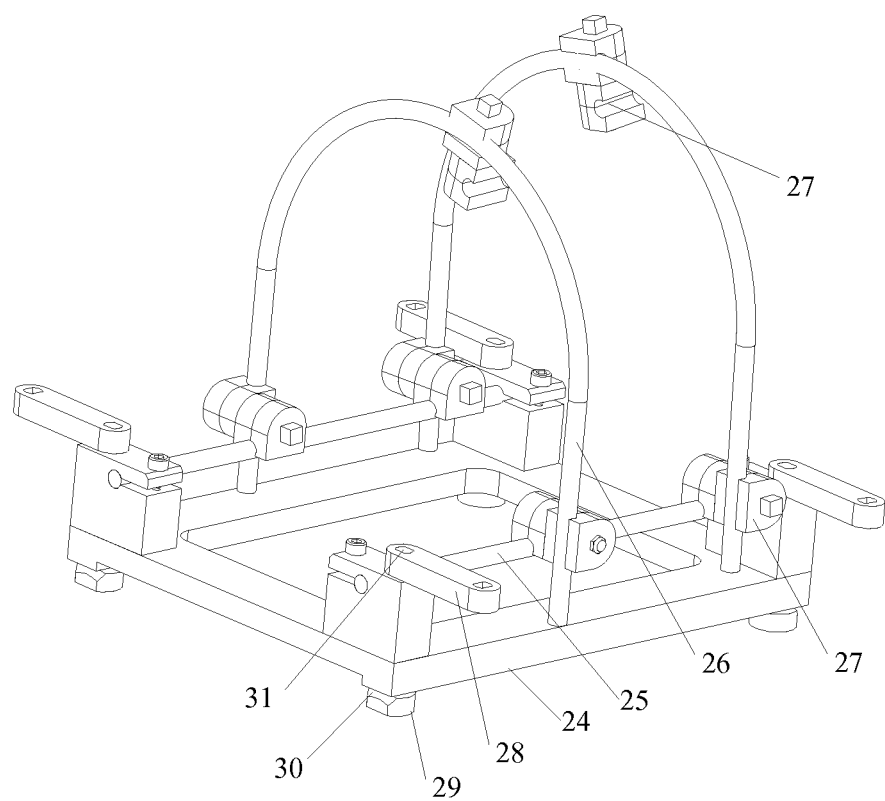
FIG. 5 is a perspective diagram of a long-bone-fixing frame provided by an embodiment of the invention.

Further, based on the above embodiment, FIG. 5 is a perspective diagram of the long-bone-fixing frame provided by the embodiment of the invention. As shown in FIG. 5, in order to improve the reduction precision, the long fixing frame 3 comprises a mounting base 24, a positioning frame is arranged on the mounting base 24, the positioning frame comprises fixing rods 26, latching-and-clamping units 27 are arranged at the end parts and the middle parts of the fixing rods 26, and the latching-and-clamping units 27 arranged at the end parts of the fixing rods 26 are in sliding fit with the mounting base 24.

Wherein, the mounting base 24 can be a plate-like member. The mounting-and-fixing plate 21 is a strip-like part, a clamping slot 22 is formed on one side of the mounting-and-fixing plate 21, jack screws are screwed on one side edge of the clamping slot 22 by through holes 23, the edge of the mounting base 24 is clamped in the clamping slot 22, and the fixed connection of the mounting base 24 and the mounting-and-fixing plate 21 is realized by pushing the jack screws onto the mounting base 24. By adopting the structure, the fast disassembly and assembly of the two long-bone-fixing frames 3 can be realized through the mounting-and-fixing plates 21, thereby facilitating the fixation of the affected limb by the doctor, increasing the operation space of the doctor and simultaneously providing convenience for the CT scan or other operations of the affected limb before the operation.

The latching-and-clamping units 27 are in sliding fit with the mounting bases 24 and can be used for regulating the relative positions of the fixing rods 26, so that the fixing rods 26 can be in the appropriate positions, and the connection with the fixing nails on the affected limb can be realized through the latching-and-clamping units 27 at the middle parts of the fixing rods.

Figure 6:
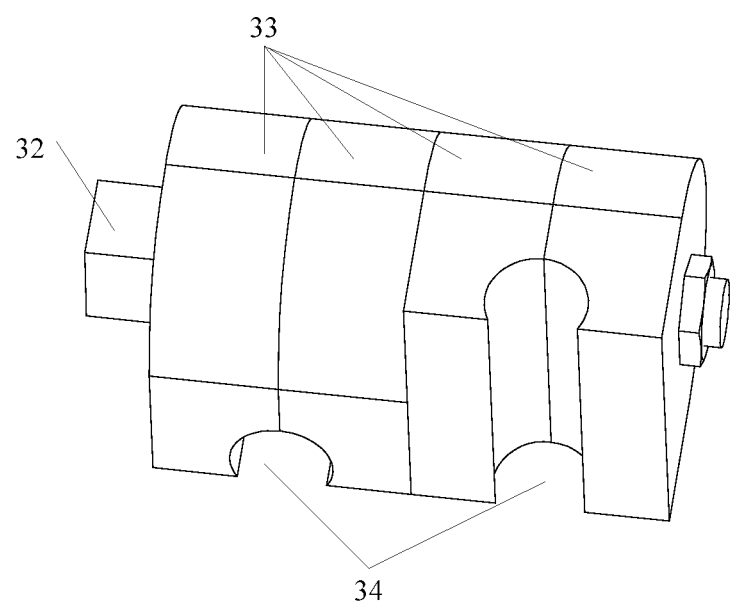
FIG. 6 is a perspective diagram of a latching-and-clamping unit provided by an embodiment of the invention.

Further, based on the above embodiment, FIG. 6 is a perspective diagram of the latching-and-clamping unit provided by the embodiment of the invention. As shown in FIG. 6, the latching-and-clamping unit 27 comprises a locking bolt 32, at least four locking and clamping blocks 33 are stacked and mounted on the locking bolt 32, and bayonets 34 are arranged at least between the first and the second locking and clamping blocks 33 and between the third and the fourth locking and clamping blocks 33. The latching-and-clamping unit has the advantages of simple structure, reliable clamping and convenience in operation.

Further, based on the above embodiment, the fixing rods are shaped like U, two sliding rods which are parallel to each other are arranged on each mounting base, the latching-and-clamping units are arranged at the two ends of the fixing rods, and the two latching-and-clamping units arranged at the two ends of the same fixing rod are separately arranged on the two sliding rods.

In order to improve the fixation reliability of the affected limb, the fixing rods 26 adopt the U-shaped structures, and the two ends of the fixing rods are fixed on the mounting bases 24 through the latching-and-clamping units 27, so that the connection between the fixing rods 26 and the mounting bases 24 is relatively firm. In actual use, two U-shaped fixing rods 26 can be arranged on each long-bone-fixing frame 3 side by side.

One of bayonets 34 of each latching-and-clamping unit 27 connected with the mounting base 24 is clamped on the sliding rod 25 of the mounting base 24, and the position can be regulated by the movement along the sliding rod 25, so that the latching-and-clamping units 27 mounted at the middle parts of the fixing rods 26 can be used for connecting with the fixing nails on the affected limb. After the positions are regulated in place, nuts at the end parts of the locking bolts 32 are tightened, thereby fixing the latching-and-clamping units 27 and the sliding rods 25 together, preventing the movement of the fixing rods 26 during the operation process and preventing affecting the reduction effect.

Figure 7:
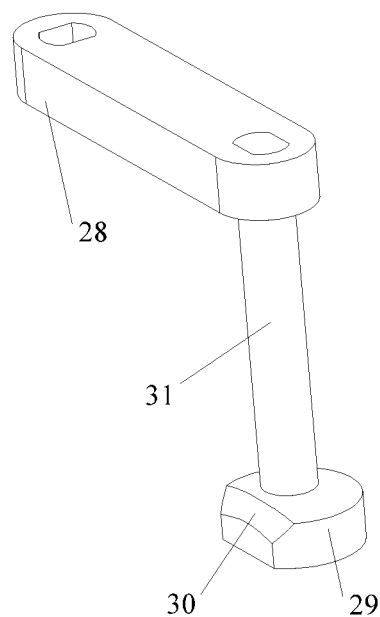
FIG. 7 is a perspective diagram of a locking shaft provided by an embodiment of the invention.
Figure 8:
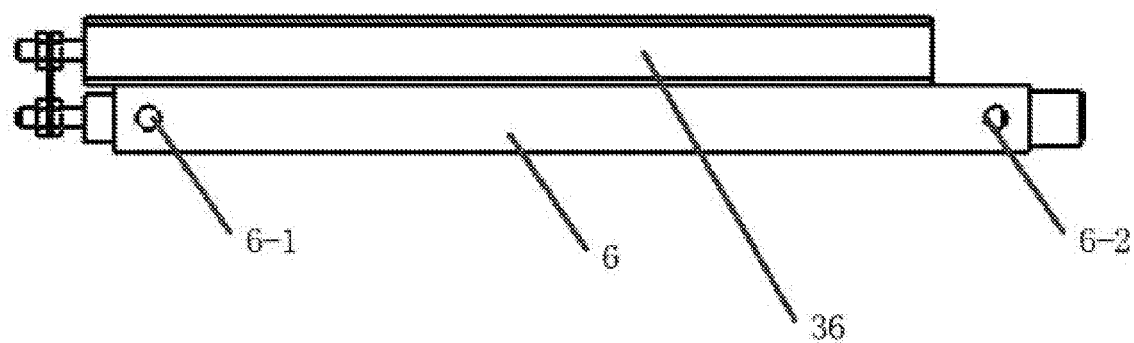
FIG. 8 is a side elevation view of a first hydraulic cylinder.
Figure 9:
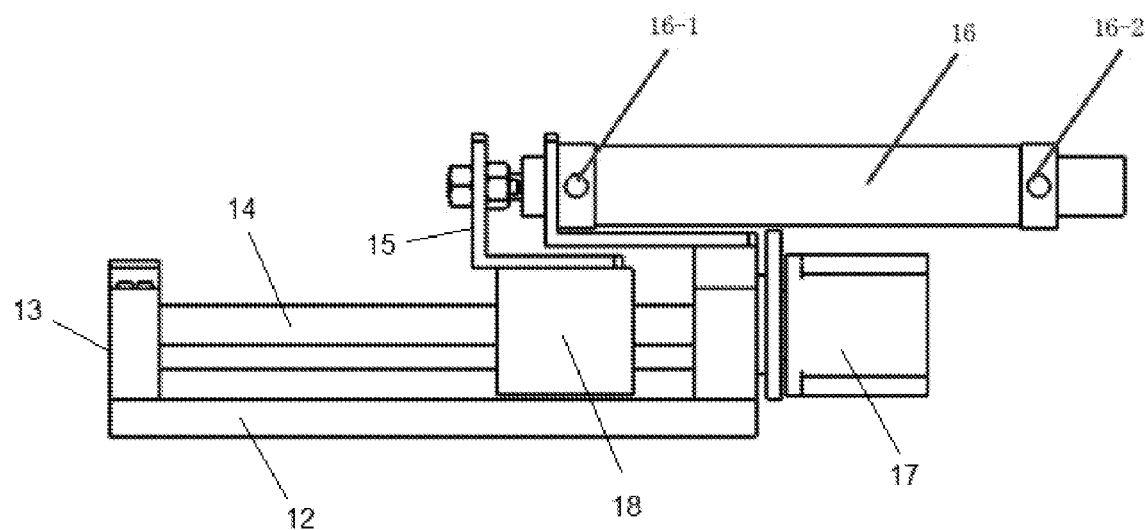
FIG. 9 is a side elevation view of the electro-hydraulic driver of FIG. 2.

Further, based on the above embodiment, FIG. 7 is a perspective diagram of a locking shaft provided by the embodiment of the invention. As shown in FIG. 7, in order to facilitate disassembly, assembly and connection of the long-bone-fixing frames 3 with the support 5 and the six-degree-of-freedom parallel robot 2, the locking shafts 31 are mounted on the mounting bases 24 in a rotating manner, one end of each locking shaft 31 is arranged on a locking block 29, locking inclined planes 30 are arranged on the locking blocks 29, and the locking inclined planes 30 face towards the mounting bases 24.

Further, based on the above embodiment, in order to facilitate disassembly, assembly and connection of the long-bone-fixing frames 3 with the support 5 and the six-degree-of-freedom parallel robot 2 by using the locking shafts 31, interface plates 11 are arranged on the support 5 and the six-degree-of-freedom parallel robot 2, the long-bone-fixing frames 3 are arranged on the interface plates 11 in one-to-one correspondence, and the interface plates 11 are sandwiched between the mounting bases 24 and the locking inclined planes 30.

Each interface plate 11 can be a rectangular flat plate. One end of each locking shaft 31 far away from the locking block 29 is connected with a handle 28, and the handle 28 can be a long circular plate piece and be in rotation stop fit with the locking shaft 31 through a flat hole and a shaft, a square hole and a shaft or other structures which are mutually matched. The locking shaft 31 is driven to rotate through the handle 28. With the rotation of the locking shaft 31, the locking inclined plane 30 also rotates synchronously, and in the rotation process, the locking inclined plane is in contact with the interface plate 11 at different heights to complete locking and unlocking. For example, when each locking inclined plane 32 is in contact with the interface plate 11 in a higher position, it is in a locking state, and at this time, the long-bone-fixing frames 3 are tightly fixed on the interface plates of the support 5 and the six-degree-of-freedom parallel robot 2 to perform the reduction operation.

Further, based on the above embodiment, in order to adapt to different using environments, a linear driver 35 for driving the support to slide up and down is arranged between the machine base 1 and the support 5. The linear driver 35 can be an electric push rod, a hydraulic cylinder or a pneumatic cylinder.

In addition, errors are unavoidable in a transmission system. In order to reduce the adverse effects caused by the errors, displacement sensors 36 are arranged on the first hydraulic cylinders 6. The motion situations of the first hydraulic cylinders 6 are detected through the displacement sensors 36 and fed back to a control system, thereby realizing closed-loop control and enabling the control system to overcome motion compensation or reduce the adverse effects caused by the errors. Namely, the control system of the reduction motion of the long-bone fracture-reduction robot comprises two parts, namely a stepping motor control part and a position sensor detection part, the stepping motor control part controls the rotation of the stepping motors and finally realizes telescoping of the first hydraulic cylinders 6, while the position sensor detection part detects the telescoping quantities of the first hydraulic cylinders 6 and corrects the telescoping quantities of the first hydraulic cylinders 6 by regulating the rotation quantities of the stepping motors by means of the stepping motor control part so as to achieve the purpose of precision control.

The long-bone fracture-reduction robot can adopt the control system with a double-layer structure comprising an upper computer and a lower computer. The upper computer is a personal computer (abbreviated as PC), with the functions of processing position information of execution mechanisms (including the stepping motors, the first hydraulic cylinders 6 and the second hydraulic cylinders 16), processing CT three-dimensional data, calculating control parameters, conveying human-computer interaction function commands and the like. The lower computer comprises a control panel of Advanced RISC Machines (abbreviated as ARM) and a stepping motor driver and is used for controlling the operation of the stepping motors and feeding the operation states of the stepping motors back to the PC in real time. The upper computer PC and the control panel of the lower computer are in wireless connection. In the driving process, a data acquisition card can feed the position information of each first hydraulic cylinder back to the upper computer periodically, and a motion control card can simultaneously monitor the abnormal situations and send the abnormal situations to the upper computer in real time.

The steps of the operation adopting the long-bone fracture-reduction robot are as follows:

1. Fixation of Fractured Bone

Two or more fixing nails are respectively driven into the proximal end and the distal end of an affected limb of a patient, the affected limb is placed between two long-bone-fixing frames 3, the positions of a fixing rod 26 and latching-and-clamping units 27 for connecting the fixing nails on the fixing rod 26, and the fixing nails are fixed onto the long-bone-fixing frames 3 so as to fix the affected limb with the long-bone-fixing frames 3, and then, the two long-bone-fixing frames 3 are fixed through mounting-and-fixing plates 24 to become a whole.

2. CT Scan

The affected limb of the patient and the two long-bone-fixing frames 3, as well as the unaffected side limb corresponding to the affected limb, are sent into a CT scanning device together, so that CT images of the bone on the affected side and the bone on the unaffected side are obtained, and the position information of the bone on the affected side in the two long-bone-fixing frames 3 is also obtained.

3. Path Planning

Mirror transformation is performed on the bone on the unaffected side, and the bone on the unaffected side after the mirror transformation is taken as a reference standard for registration of the bone on the affected side. Characteristic regions for registration are respectively selected at the two ends of the bone on the affected side and the unaffected bone, automatic registration is utilized, and a manual fine regulation method is further combined, thereby enabling the two ends of the bone on the affected side to coincide with the two ends of the unaffected bone, and obtain a transformation matrix of relative changes of poses at the two ends of the bone on the affected side after coincidence. After that, some points on the two long-bone-fixing frames 3 are taken as characteristic points, the coordinates of these characteristic points in a coordinate space of the CT images are known, the coordinates in the coordinate space of the long-bone fracture-reduction robot can also be obtained by calculation, and a mapping relation between the coordinates in the coordinate space of the CT images and the coordinates in the coordinate space of the robot is calculated, so that the pose transformation matrix of the long-bone-fixing frame to be moved relative to the still long-bone-fixing fame 3 is calculated, and control parameters of motion of the long-bone fracture-reduction robot are obtained. A reasonable path of motion of the long-bone fracture-reduction robot is further planned out.

4. Traction Reduction

The affected limb of the patient and the two long-bone-fixing frames 3 are correspondingly connected with a support 5 and a six-degree-of-freedom parallel robot 2. One of the long-bone-fixing frames 3 is fixedly connected with an interface plate 11 on the six-degree-of-freedom parallel robot 2, the other bone fixing frame 3 is fixedly connected with the support 5, and the mounting-and-fixing plates 24 are detached after the connection, so that the two ends of the affected limb can relatively move with the six-degree-of-freedom parallel robot 2. An upper computer controls the six-degree-of-freedom parallel robot 2 to perform traction reduction operation on the affected limb according to the planned motion path.

5. Reduction and Fixation

After the affected limb achieves a reduction standard, the fixing rods 26 are utilized to relatively fix the proximal end and the distal end of the affected limb through support rods, and the affected limb after fixation is moved out of the two long-bone-fixing frames 3.

It can be seen that, by adopting the long-bone fracture-reduction robot, the following advantages can be realized:

1) The minimally invasive long bone fracture reduction function is realized under a closed state, and the long-bone fracture-reduction robot is used for performing the reduction operation instead of the doctor, so that the precision is high, and the trauma is small. The traditional open type fracture reduction way is changed, the occurrence of situations of delayed healing, bone non-union, infection and the like at a fracture part is reduced, and the operative errors and other problems caused by operative fatigue of the doctor can be prevented.

2) The series-parallel hybrid mechanism constituted by electro-hydraulic drivers 4 and the six-degree-of-freedom parallel robot 2 is adopted, so that six degrees of freedom are realized, and the advantages of large working space and good flexibility of a series mechanism, as well as high positioning precision, large loading capacity, compact structure, high rigidity and the like of a parallel mechanism are integrated. The requirements on the working space, the degrees of freedom, the rigidity and the like for fracture reduction are met.

3) The long-bone-fixing frames 3 have the functions of preliminary reduction and fixation of the affected limb and can be mutually connected or split with the six-degree-of-freedom parallel robot 2 and the support 5, thereby facilitating the fixation of the series mechanism and the affected limb by the doctor, increasing the operation space of the doctor and simultaneously providing the convenience for the CT scan or other operations of the affected limb before the operation.

4) The vertical structure is adopted, the six-degree-of-freedom parallel robot 2 and the support 5 are positioned below the affected limb, thereby reducing the inference on the affected limb and simultaneously increasing the working space. The pose of the support is regulated through an electric push rod 35 to better adapt to the patient.

Although the embodiments of the invention are described in detail in combination with the accompanying drawings, it should be understood that the implementations described above are only used for illustrating the invention and are not construed as limiting the invention. For those of skill in the art, various modifications and changes can be made to the above implementations without deviating from the spirit or the scope of the invention. Thus, the scope of the invention is only defined by the appended claims and the equivalent contents thereof.

We claim:

1. A long-bone fracture-reduction robot, comprising:
a machine base;
a support capable of moving up and down slidably connected on the machine base;
a plurality of electro-hydraulic drivers;
a six-degree-of-freedom parallel robot arranged on the support, the six-degree-of-freedom parallel robot comprising:
a plurality of first hydraulic cylinders, each comprising a first hydraulic fluid port and a second hydraulic fluid port, the number of first hydraulic cylinders being equal to the number of electro-hydraulic drivers, wherein each first hydraulic cylinder is in one-to-one driving connection with a corresponding electro-hydraulic driver, and
a first long-bone-fixing frame, wherein the first long-bone-fixing frame is coupled to the six-degree-of-freedom parallel robot, and wherein the plurality of first hydraulic cylinders are each connected to the first long-bone-fixing frame.

2. The long-bone fracture-reduction robot according to claim 1, wherein each electro-hydraulic driver comprises:
a driving motor;
a second hydraulic cylinder including a piston rod, a first hydraulic fluid port, and a second hydraulic fluid port;
a lead screw drivably connected to the driving motor;
a sliding block screwed on the lead screw and fixedly coupled to the piston rod of the second hydraulic cylinder;
wherein each of the first hydraulic cylinders is in one-to-one connection a corresponding second hydraulic cylinder,
wherein the first hydraulic fluid port of each first hydraulic cylinder is in one-to-one connection with and in communication with the first hydraulic fluid port of the corresponding second hydraulic cylinder, and
wherein the second hydraulic fluid port of each first hydraulic cylinder is in communication with the second hydraulic fluid port of the corresponding second hydraulic cylinder.

3. The long-bone fracture-reduction robot according to claim 1, further comprising a second long-bone-fixing frame, the second long-bone-fixing frame being coupled to the support.

4. The long-bone fracture-reduction robot according to claim 3, wherein the first and second long-bone-fixing frames are arranged to be side by side, and wherein each of the first and second long-bone-fixing frames is fixedly connected to a corresponding mounting-and-fixing plate.

5. The long-bone fracture-reduction robot according to claim 3, wherein each long-bone-fixing frame comprises a mounting base, wherein positioning frames are arranged on the mounting base, the positioning frames including fixing rods, wherein latching-and-clamping units are arranged at the end parts and the middle parts of the fixing rods, and wherein the latching-and-clamping units arranged at the end parts of the fixing rods are in sliding fit with the mounting bases.

6. The long-bone fracture-reduction robot according to claim 5, wherein each latching-and-clamping unit comprises a locking bolt, wherein at least four locking and clamping blocks are stacked and mounted on each locking bolt, and wherein bayonets are arranged at least between the first and the second locking and clamping blocks and between the third and the fourth locking and clamping blocks.

7. The long-bone fracture-reduction robot according to claim 5, wherein the fixing rods are U-shaped, wherein two sliding rods are parallel to each other and are arranged on each mounting base, wherein the latching-and-clamping units are arranged at the two ends of the fixing rods, and wherein the two latching-and-clamping units arranged at the two ends of the same fixing rod are separately arranged on the two sliding rods.

8. The long-bone fracture-reduction robot according to claim 5, wherein locking shafts are mounted on the mounting bases in a rotating manner, one end of each locking shaft being arranged on a locking block, and wherein the locking block has locking inclined planes facing towards the mounting bases.

9. The long-bone fracture-reduction robot according to claim 8, wherein interface plates are arranged on the support and the six-degree-of-freedom parallel robot, wherein the long-bone-fixing frames are arranged on the interface plates in one-to-one correspondence, and wherein the interface plates are sandwiched between the mounting bases and the locking inclined planes.

10. The long-bone fracture-reduction robot according to claim 3, wherein a linear driver for driving the support to slide up and down is arranged between the machine base and the support, and wherein displacement sensors are arranged on the first hydraulic cylinders.

* * * * *